(12) United States Patent
Dellock et al.

(10) Patent No.: US 10,377,351 B2
(45) Date of Patent: Aug. 13, 2019

(54) DISPLAY FOR A VEHICLE

(71) Applicant: Ford Global Technologies, LLC, Dearborn, MI (US)

(72) Inventors: Paul Kenneth Dellock, Northville, MI (US); Stuart C. Salter, White Lake, MI (US); David Brian Glickman, Southfield, MI (US); Annette Lynn Huebner, White Lake, MI (US); Venkatesh Krishnan, Canton, MI (US)

(73) Assignee: FORD GLOBAL TECHNOLOGIES, LLC, Dearborn, MI (US)

( * ) Notice: Subject to any disclaimer, the term of this patent is extended or adjusted under 35 U.S.C. 154(b) by 0 days.

(21) Appl. No.: 15/636,006

(22) Filed: Jun. 28, 2017

(65) Prior Publication Data
US 2019/0001933 A1    Jan. 3, 2019

(51) Int. Cl.
| | |
|---|---|
| B60S 1/60 | (2006.01) |
| A61L 2/08 | (2006.01) |
| A61L 2/10 | (2006.01) |
| A61L 2/24 | (2006.01) |
| B08B 7/00 | (2006.01) |
| G02F 1/1333 | (2006.01) |
| G06F 3/00 | (2006.01) |

(Continued)

(52) U.S. Cl.
CPC ............ *B60S 1/603* (2013.01); *A61L 2/088* (2013.01); *A61L 2/10* (2013.01); *A61L 2/24* (2013.01); *B08B 7/0035* (2013.01); *B08B 7/0057* (2013.01); *G02B 27/0006* (2013.01); *G02F 1/13338* (2013.01); *G06F 3/00* (2013.01); *A61L 2202/11* (2013.01); *A61L 2202/14* (2013.01); *A61L 2202/17* (2013.01); *B60S 1/66* (2013.01); *G02F 1/133308* (2013.01)

(58) Field of Classification Search
USPC ..................................... 250/454.11
See application file for complete search history.

(56) References Cited

U.S. PATENT DOCUMENTS

| | | | |
|---|---|---|---|
| 6,690,268 B2 * | 2/2004 | Schofield | ................ B60C 23/00 340/438 |
| 8,147,971 B2 | 4/2012 | Van Herpen | |

(Continued)

FOREIGN PATENT DOCUMENTS

| | | |
|---|---|---|
| CN | 202905045 U | 4/2013 |
| EP | 0368450 A2 | 5/1990 |

(Continued)

OTHER PUBLICATIONS

Search Report from United Kingdom Intellectual Property Office dated Dec. 14, 2018 regarding Application No. GB1810513.0 (7 pages).

(Continued)

*Primary Examiner* — Phillip A Johnston
(74) *Attorney, Agent, or Firm* — Frank A. MacKenzie; Bejin Bieneman PLC (57) ABSTRACT

An interior cleaning system for a vehicle is disclosed. The system may include a display, and the display may include: a screen that includes a cover having a light-sensitive coating on an outwardly-facing side thereof; and a bezel having a lamp, wherein, when actuated, light from the lamp activates the coating.

20 Claims, 7 Drawing Sheets

(51) Int. Cl.
  *G02B 27/00* (2006.01)
  *B60S 1/66* (2006.01)

(56) References Cited

U.S. PATENT DOCUMENTS

| | | | |
|---|---|---|---|
| 8,951,614 B2* | 2/2015 | Collins | G01N 35/00732 347/139 |
| 9,785,192 B1 | 10/2017 | Cheng et al. | |
| 2003/0073042 A1* | 4/2003 | Cernigliaro | G03F 7/0007 430/321 |
| 2004/0160762 A1 | 8/2004 | Fuwausa | |
| 2006/0087826 A1 | 4/2006 | Anderson | |
| 2006/0158735 A1* | 7/2006 | Tonar | B60R 1/0602 359/507 |
| 2008/0158510 A1 | 7/2008 | Tant et al. | |
| 2010/0148695 A1 | 6/2010 | Hsieh | |
| 2011/0256019 A1 | 10/2011 | Gruen et al. | |
| 2013/0045132 A1 | 2/2013 | Tumanov | |
| 2014/0286048 A1 | 9/2014 | Riello et al. | |
| 2015/0286085 A1 | 10/2015 | Davis et al. | |
| 2016/0357281 A1 | 12/2016 | Fleizach et al. | |
| 2017/0224853 A1 | 8/2017 | Jay | |
| 2018/0031740 A1* | 2/2018 | Alarcon | F21S 41/28 |

FOREIGN PATENT DOCUMENTS

| | | |
|---|---|---|
| JP | 2000010491 A | 1/2000 |
| JP | 2000352947 A | 12/2000 |
| JP | 2001096167 A | 4/2001 |
| JP | 2004219969 A | 8/2004 |
| JP | 2007315954 A | 12/2007 |
| JP | 2007331546 A | 12/2007 |
| JP | 2012254673 A | 12/2012 |
| KR | 100740903 B1 | 7/2007 |
| WO | WO 03033037 A | 4/2003 |
| WO | 2017204774 A1 | 11/2017 |

OTHER PUBLICATIONS

Search Report from United Kingdom Intellectual Property Office dated Dec. 24, 2018 regarding Application No. GB1810511.4 (9 pages).

Non-Final Office Action dated May 23, 2019 for U.S. Appl. No. 15/636,024 (37 pages).

* cited by examiner

DISPLAY FOR A VEHICLE

BACKGROUND

During normal use, dust, fingerprints, and other fluids can adhere to the surfaces of a vehicle display. To clean such contaminants, the user of the vehicle conventionally manually applies a soft cloth which may or may not have a cleaning solution thereon.

DETAILED DESCRIPTION

An interior cleaning system for a vehicle is described that includes a display having a bezel that includes a lamp which directs light toward a screen of the display to clean a surface thereof. According to one example, the display includes: a screen comprising a cover having a light-sensitive coating on an outwardly-facing side thereof; and a bezel having a lamp, wherein, when actuated, light from the lamp activates the coating.

According to the at least one example set forth above, when the lamp is actuated, light is directed axially and radially-inwardly from the bezel and toward the cover.

According to the at least one example set forth above, the lamp emits an ultraviolet wavelength.

According to the at least one example set forth above, the coating comprises a material which undergoes a chemical reaction in a presence of light from the lamp.

According to the at least one example set forth above, the screen comprises an electronics portion that includes: the cover, a capacitive or resistive film, a liquid crystal display (LCD), and a backlight, wherein the film and LCD are sandwiched between the cover and backlight.

According to the at least one example set forth above, the coating comprises titanium dioxide ($TiO_2$), wherein the lamp emits light at a wavelength within 310-390 nanometers (nm).

According to the at least one example set forth above, the lamp comprises a plurality of light sources located in the bezel.

According to the at least one example set forth above, the bezel comprises a plurality of members, wherein each member comprises at least one of the plurality of light sources.

According to the at least one example set forth above, the screen comprises a matrix of user-touch regions.

According to the at least one example set forth above, a first member comprises a selectively-actuatable first light source and a selectively-actuatable second light source, a second member comprises a selectively-actuatable third light source and a selectively-actuatable fourth light source, wherein, when selectively-actuated, the second and third light sources illuminate the same user-touch region of the screen.

According to the at least one example set forth above, when selectively-actuated, the first light source illuminates a different user-touch region of the screen and the fourth light source illuminates another, different user-touch region of the screen.

According to the at least one example set forth above, each of the plurality of members comprise at least two light sources, wherein the matrix comprises four user-touch regions, wherein, when selectively-actuated, the respective light sources of each pair of adjacently-located members illuminates one of the user-touch regions.

According to the at least one example set forth above, at least one of the plurality of light sources comprises a plurality of light elements.

According to another illustrative example, at least two of the plurality of light elements emit light in different wavelengths, wherein the wavelengths comprise: 310-390 nanometers (nm), 400-410 nm, 670-700 nm, and 700-800 nm.

According to the at least one example set forth above, when actuated, light power, incident at the coating, from each of the respective light sources is at least 1 milli-Watt per square centimeter ($mW/cm^2$).

According to the at least one example set forth above, the screen is a touchscreen.

According to the at least one example set forth above, the lamp comprises a light source and an optic positioned relative to the light source to direct light emitted from the source toward the surface.

According to the at least one example set forth above, an interior cleaning system for a vehicle is disclosed that includes the display described above, wherein the lamp comprises a plurality of light sources; and a computer that includes: a processor, and memory storing instructions executable by the processor, the instructions including: to selectively-actuate the plurality of light sources.

According to the at least one system example set forth above, a manual switch is disclosed, which, when actuated, triggers at least one of the plurality of light sources to illuminate.

According to the at least one system example set forth above, an occupancy detection system is disclosed that is coupled to the computer that provides an indication of an occupancy state, wherein the instructions further include: to temporarily inhibit actuation of the plurality of light sources based on the occupancy state being occupied when an ambient light is less than a threshold.

According to the at least one example, a computer is disclosed that is programmed to execute any combination of the examples set forth above.

According to the at least one example, a computer program product is disclosed that includes a computer readable medium storing instructions executable by a computer processor, wherein the instructions include any combination of the instruction examples set forth above.

Figure 1:
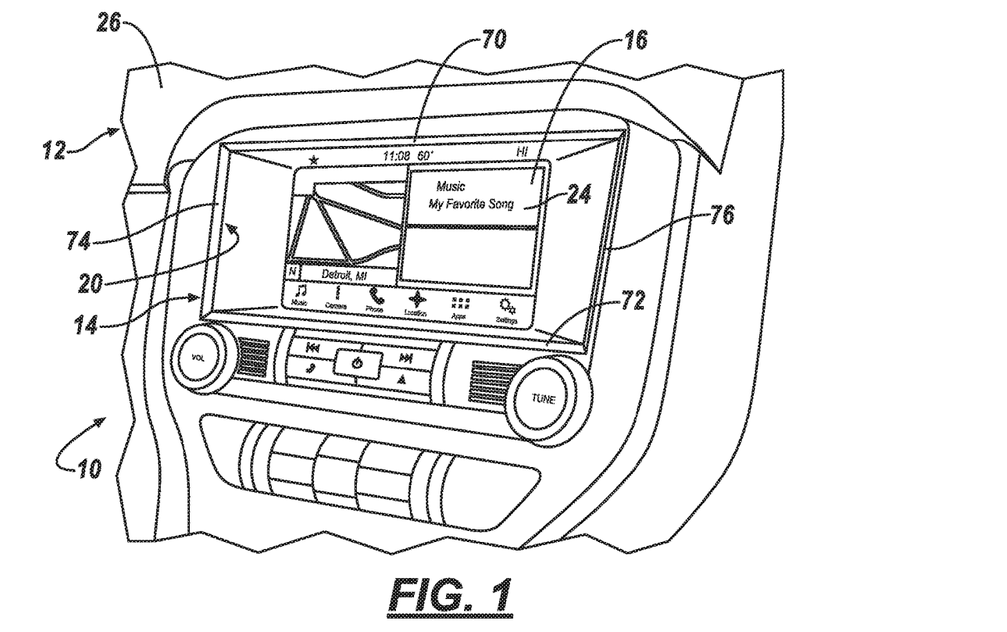
FIG. 1 illustrates an interior cleaning system that includes a display carried by an instrument panel of a vehicle.
Figure 2:
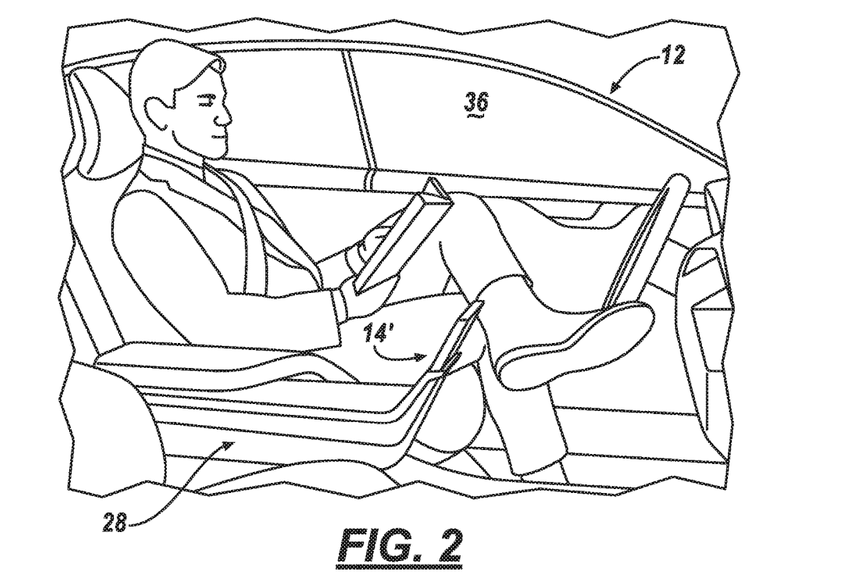
FIG. 2 illustrates an occupant in a cabin of the vehicle and a similar display carried by a center console.

Now turning to the figures, wherein like numerals indicate like parts throughout the several views, there is shown an interior cleaning system 10 for a vehicle 12 that comprises a display 14 that includes a screen 16 having a light-sensitive coating 18 and a bezel 20 having a lamp 22 which emits light at a frequency that activates the coating 18 to clean or sanitize a surface 24 of the screen. The display 14 may be carried by a vehicle instrument panel 26 (e.g., as shown in FIG. 1) or may be located elsewhere (e.g., such as display 14' coupled to a center console 28, as shown in FIG. 2). In at least some examples, the screen 16 is a touchscreen which may be used by a number of different users (e.g., consider examples where vehicle 12 is an autonomous taxi or rideshare vehicle). As described more below, when actuated, the lamp 22 of the display 14 may project light which kills or neutralizes living organic matter on the surface 24 of screen 16 (e.g., kills bacteria and viruses on the screen from sweat, saliva, etc. of the different users). According to one non-limiting example, the light-sensitive coating 18 may comprise titanium dioxide and the frequency emitted by lamp 22 may be in the ultraviolet (UV) band. Hence, the UV light may kill the living organic matter, while the titanium dioxide (in the presence of UV light) may react with carbon-based matter located on the surface 24 of screen 16 (e.g., such as bacteria, viruses, saliva, sweat, and other human bodily fluids) yielding a water vapor and carbon dioxide gas by-product. As described below, other light-sensitive coatings and/or other light wavelengths could be used instead.

Vehicle 12 is shown as a passenger car; however, vehicle 12 could also be a truck, sports utility vehicle (SUV), recreational vehicle, bus, train, marine vessel, aircraft, or the like that includes the interior cleaning system 10. Vehicle 12 may be operated in any one of a number of autonomous modes. In at least one example, vehicle 12 may operate as an autonomous taxi, a ride-sharing vehicle, an autonomous school bus, or the like—e.g., operating in a fully autonomous mode (e.g., a level 5), as defined by the Society of Automotive Engineers (SAE) (which has defined operation at levels 0-5). For example, at levels 0-2, a human driver monitors or controls the majority of the driving tasks, often with no help from the vehicle 12. For example, at level 0 ("no automation"), a human driver is responsible for all vehicle operations. At level 1 ("driver assistance"), the vehicle 12 sometimes assists with steering, acceleration, or braking, but the driver is still responsible for the vast majority of the vehicle control. At level 2 ("partial automation"), the vehicle 12 can control steering, acceleration, and braking under certain circumstances without human interaction. At levels 3-5, the vehicle 12 assumes more driving-related tasks. At level 3 ("conditional automation"), the vehicle 12 can handle steering, acceleration, and braking under certain circumstances, as well as monitoring of the driving environment. Level 3 may require the driver to intervene occasionally, however. At level 4 ("high automation"), the vehicle 12 can handle the same tasks as at level 3 but without relying on the driver to intervene in certain driving modes. At level 5 ("full automation"), the vehicle 12 can handle all tasks without any driver intervention.

Interior cleaning system 10 may include an occupancy detection system 30, a vehicle powertrain system 32, the display 14 (described in detail below), and a computer 40 which may form part of the display 14 (e.g., within a common module) or which may be coupled electrically thereto. Occupancy detection system 30 and powertrain system 32 may provide relevant data to computer 40 so that computer 40 may manage the cleaning of display 14; in addition, systems 30-32 may facilitate vehicle 12 operating in a fully autonomous mode.

Occupancy detection system 30 may comprise at least one computer 34 electrically coupled to a number of sensors (e.g., not shown). Computer 34 may receive data from seat-belt sensors, seat pressure sensors, cabin cameras or imaging sensors (e.g., aimed at vehicle seating to detect occupancy), proximity sensors, and the like. In general, computer 34 may analyze the data from one or more sensors to determine whether a cabin 36 of vehicle 12 is empty or occupied, e.g., using techniques known to those skilled in the art. Further, computer 34 may provide an output (e.g., an analog or digital signal) to interior cleaning system 10 that indicates the cabin state (e.g., 'empty' or 'occupied'). Computer 34 further may indicate whether an occupant is currently ingressing or egressing the cabin using door sensors, vision sensors, proximity sensors, or the like.

Powertrain system 32 may comprise at least one computer 38 electrically coupled to a vehicle engine (not shown) and a vehicle transmission (not shown). According to at least one example, computer 38 may provide, to the interior cleaning system 10, an output (e.g., an analog or digital signal) indicating a state of the engine. For example, when the engine is running, the state may be ON, and when the engine is not running, the state may be OFF. As explained more below, in at least one example, computer 40 may clean display 14 when the vehicle engine state is ON. The term vehicle engine should be construed broadly to include a combustion engine, a hybrid electric engine, an electric engine or motor(s), a solar-electric engine, or the like.

Interior cleaning system 10 of vehicle 12 may include other systems (not shown) as well which facilitate operation of the vehicle in a fully autonomous mode. Non-limiting examples of systems related to autonomous driving include one or more vision and/or imaging systems, additional sensing systems (e.g., in addition to occupancy detection system 30), one or more wireless vehicle communication systems, a vehicle steering system, a vehicle braking system, one or more vehicle safety systems, and the like. In some examples, these systems related to autonomous driving may be controlled collectively by a master computing device; in other examples, no master computing device exists (e.g., instead the systems interact directly or via a mesh communication network). Thus, for example, each system related to autonomous driving may comprise one or more system computing devices which interact with one another to control autonomous or driver-less vehicle operation. Consequently, according to one example, the vehicle 12 may be controlled collectively by the systems to drive in a fully autonomous mode to pick up a vehicle user (e.g., according to a request sent from the user to the vehicle 12). Once the user is in vehicle 12, the systems related to autonomous driving may cause the vehicle 12 deliver the user to a predetermined location (e.g., according to his/her request). While in the vehicle, neither the user or other occupants may need to exhibit control over any combination of the systems described above. According to one example, as described more below, the user may enter destination data into the display 14 and/or while traveling from origination location to destination location, the user may use the display to receive information services, entertainment services, the like, or any combination thereof. The term user, as used herein, means a licensee or other authorized person within vehicle 12; further, the term user (within vehicle 12) and occupant may be used interchangeably.

Computer 40 may comprise at least one processor 42 and memory 44 coupled to the processor 42, wherein memory 44 stores instructions executable by the processor 42. For example, processor 42 can be any type of device capable of processing electronic instructions, non-limiting examples including a microprocessor, a microcontroller or controller, an application specific integrated circuit (ASIC), etc.—just to name a few. In general, computer 40 may be programmed to execute digitally-stored instructions, which may be stored in memory 44, which enable the computer 40, among other things, to receive an indication that the vehicle engine state is ON (e.g., from powertrain system 32) and to receive an indication that the vehicle is in an unoccupied state (e.g., from occupancy detection system 30), and based on these indications, to actuate the lamp 22 (e.g., causing light from the lamp to be directed toward the surface 24 of the screen 16, thereby sanitizing the surface 24). Computer 40 may be programmed to carry out other instructions as well—e.g., including selectively controlling one or more light sources (discussed below) of lamp 22, controlling the wavelengths of light emitted from the lamp 22, actuating the lamp 22 based on a cleaning schedule, actuating the lamp 22 based on a quantity of user-touches, actuating the lamp 22 based on a capacitance of a contact region of screen 16, and actuating the lamp 22 based on a manual switch actuation (e.g., by an authorized vehicle service technician), just to name a few non-limiting examples.

Memory 44 may include any non-transitory computer usable or readable medium, which may include one or more storage devices or articles. Exemplary non-transitory computer usable storage devices include conventional computer system RAM (random access memory), ROM (read only memory), EPROM (erasable, programmable ROM), EEPROM (electrically erasable, programmable ROM), as well as any other volatile or non-volatile media. Non-volatile media include, for example, optical or magnetic disks and other persistent memory. Volatile media include dynamic random access memory (DRAM), which typically constitutes a main memory. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, or any other medium from which a computer can read. As discussed above, memory 44 may store one or more computer program products which may be embodied as software, firmware, or the like.

Figure 3:
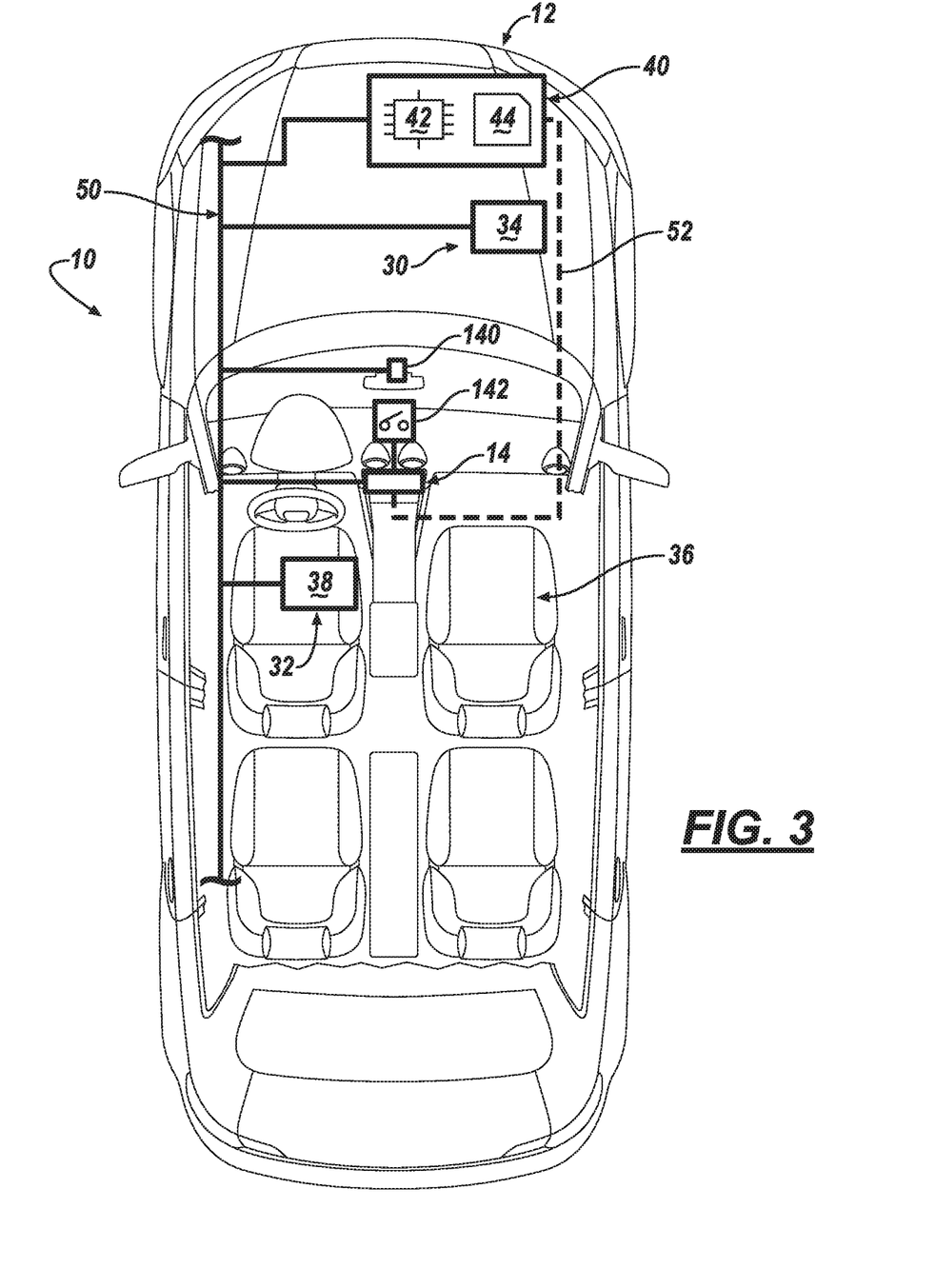
FIG. 3 is a schematic diagram of the vehicle illustrating a network connection coupling the display of FIG. 1 to one or more vehicle system computers.

FIG. 3 illustrates a wired and/or wireless vehicle network connection 50 which enables, among other things, communication between computer 34 (of occupancy detection system 30), computer 38 (of powertrain system 32), and computer 40 and/or display 14. In at least one example, the connection 50 includes one or more of a controller area network (CAN) bus, Ethernet, Local Interconnect Network (LIN), a fiber optic connection, a Bluetooth or Bluetooth Low Energy (BLE) connection, a Wi-Fi or Wi-Fi Direct connection, or the like. Other examples also exist. Aspects of connection 50 may be standardized; other aspects may be proprietary; and of course, combinations thereof are possible as well. Network connection 50 may facilitate intra-vehicular system communication—e.g., enabling display computer 40 to receive data regarding, e.g., engine state (e.g., from computer 38) and/or vehicle occupancy state (e.g., from computer 34). FIG. 3 further illustrates that connection 50 may comprise discrete wired or wireless connections as well. For example, computer 40 may be communicatively coupled to display 14 by bus 50, by discrete connection 52, or a combination thereof.

Turning now to display 14, the display may comprise a multi-layer screen 16 overlaid by (or abutting) bezel 20—e.g., at a periphery 54 thereof. The screen 16 may be a touchscreen; however, this is not required. For example, screen 16 may be a capacitive touchscreen, a resistive touchscreen, or the like. For purposes of illustration only, and not intending to be limiting, an example of a capacitive touchscreen is described below.

Figure 4:
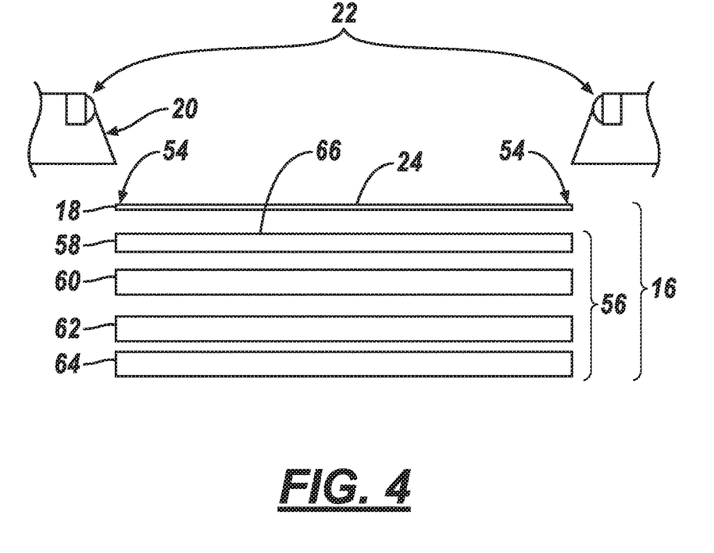
FIG. 4 illustrates an exploded, schematic view of a screen of the display.

Screen 16 may comprise the light-sensitive coating 18 and an electronics portion 56 that includes: a lens or cover 58, a film 60 (e.g., a capacitive or resistive film), a liquid crystal display (LCD) 62, and a backlight 64. The cover 58 may be a transparent sheet of plastic, resin, glass, etc. which protects the film 60, LCD 62, and backlight 64 therebeneath. The capacitive film 60 may comprise an electrical circuit that includes a plurality of capacitive elements (not shown) responsive to the electrical energy carried by a human fingertip when the user's fingertip touches the cover 58. LCD 62 can include an electrically-modulated optical device using liquid crystal to provide an image outwardly (i.e., into the cabin 36) through the cover 58 when light is projected from the backlight 64 (e.g., which may comprise an optical waveguide, a light source, a driver circuit for the light source, etc.—none of which are shown). According to one arrangement, the film 60 and LCD 62 are sandwiched between the cover 58 and backlight 64. In general, the backlight 64 provides light axially-outwardly (toward cover 58). This light illuminates the LCD 62 which displays any suitable computer-controlled graphics—e.g., enabling the screen 16 to function as an output device. When the user touches the coating 18 and/or cover 58, the capacitive film 60 identifies the contact or touch, as well as gestures made through the user-touch(es) indicating user commands, selections, etc.—e.g., enabling the screen 16 to function as an input device. The electronics portion 56 may comprise other layers and/or other suitable elements, the construction and operation of which will be appreciated by those skilled in the relevant art.

Light-sensitive coating 18 may be applied to an outwardly-facing side 66 of cover 58 using vapor deposition or any other suitable technique. And a thickness of the coating 18 may not substantially interfere with the input and output functions of screen 16. As used herein, a light-sensitive coating is any coating, layer, or film locating on an outermost surface of the electronics portion 56 of screen 16 which, when in the presence of light emitted from the bezel lamp 22 participates in a chemical reaction. As used herein, a chemical reaction is a process wherein at least one material of the coating 18 changes or is converted to a different substance (a different type of material). As explained more below, in at least one example, this chemical reaction may require multiple reactants (e.g., the coating 18 plus some carbon or other organic matter) to yield a new product (e.g., the different substance).

According to at least one example, the light-sensitive coating 18 comprises titanium dioxide ($TiO_2$) having any suitable thickness. According to one example, the $TiO_2$ coating 18 does not degrade, more than 10%, the transmissivity of light received by the user from the backlight 64 and further does not change, more than 5%, the capacitive response (in film 60) resulting from user-touches; however, this is merely one example, and other examples exist. In this implementation, in the presence of light from the bezel 20, the $TiO_2$ coating 18 (a reactant) plus an organic material on the surface 24 of the coating 18 (e.g., a second reactant) may yield water ($H_2O$) and carbon dioxide ($CO_2$) (the products of the chemical reaction). Titanium dioxide is merely one example of coating 18; other materials could be used instead.

Bezel 20 may include any suitable frame that extends around the periphery 54 of screen 16. Thus, in at least one example, the bezel 20 may comprise a first or upper member 70, a second or leg member 76, a third or lower member 72, and a fourth or leg member 74, wherein the upper, lower, and leg members 70-76 are coupled to one another end-to-end and have rectangular arrangement (e.g., see FIG. 6)—e.g., member 70 adjacent to member 76, member 76 adjacent to member 72, member 72 adjacent to member 74, and member 74 adjacent to member 70. Other bezel shapes are also possible—e.g., including one member examples (e.g., a curved member forming an oval or an elliptical shape in front of screen 16), and other multi-member examples (e.g., including triangular, trapezoidal, rhomboid, hexagonal, octagonal, etc. shapes), just to name a few non-limiting examples.

Figure 5:
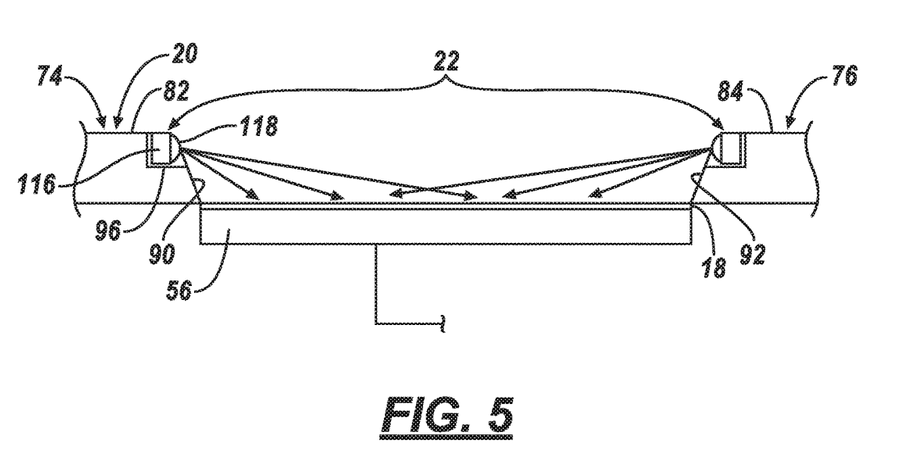
FIG. 5 illustrates a schematic, sectional view of the display.

In one example, each member 70-76 may comprise a first or outwardly-facing face 78, 80, 82, 84 (respectively) and a second or axially-extending face 86, 88, 90, 92 (respectively). The second faces 86-92 respectively may extend axially and radially-outwardly from surface 24 of screen 16 to respective first faces 78-84. (See also FIG. 5) showing second faces 90, 92 sloping between first faces 82, 84 respectively, and screen 16.) First faces 78-84 may be parallel to the surface 24; however, this is not required.

Figure 6:
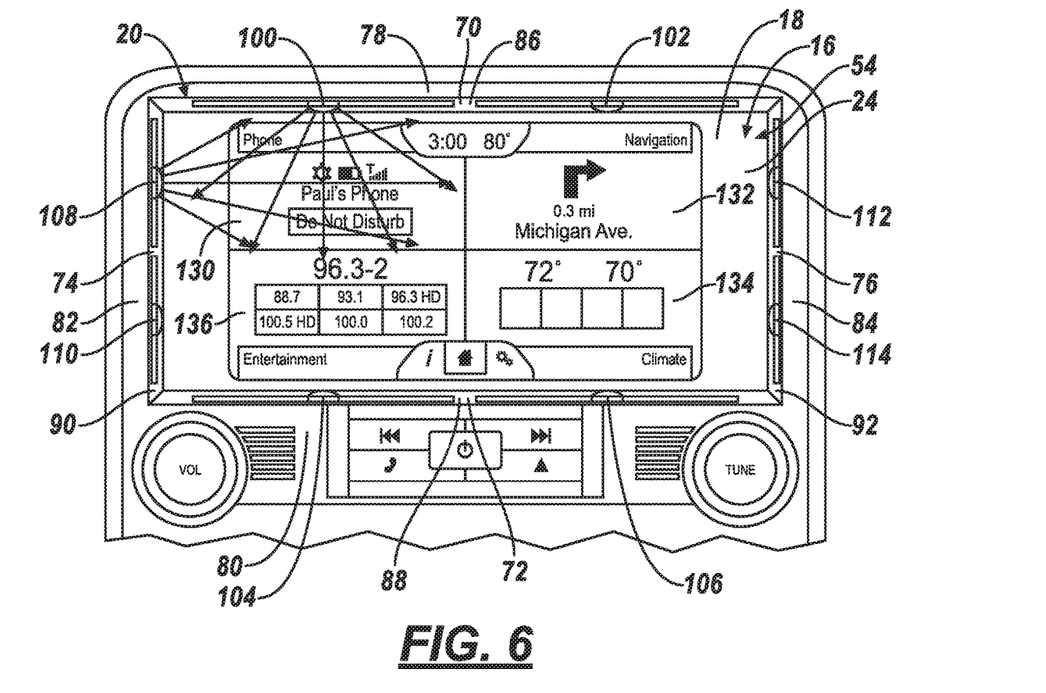
FIG. 6 is a front, schematic view of an exemplary display, illustrating a lamp in the bezel of the display comprising a plurality of light sources and graphics which divide the screen into a plurality of user-touch regions.

One or more members of bezel 20 may have a cavity 96 sized to carry lamp 22 or light source(s) thereof, as explained more below. For example, lamp 22 may comprise a plurality of light sources. For example, FIG. 6 illustrates each member 70-76 carrying a pair of light sources 100-102, 104-106, 108-110, and 112-114, respectively. Each light source 100-114 includes at least one light element and also may comprise an optic.

Figure 6A:
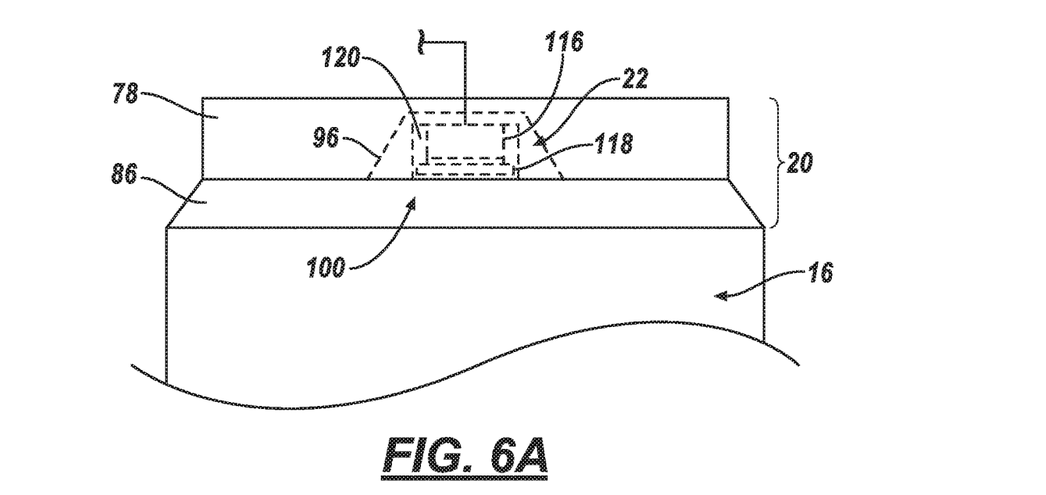
FIG. 6A is a schematic diagram of an exemplary light source.

According to one example, each light source 100-114 is similar or identical; therefore, only one will be described herein. FIG. 6A illustrates a schematic view of light source 100 within cavity 96—the light source comprising a light element 116 and optic 118 carried by a printed circuit board (PCB) 120, wherein the optic 118 is configured, as well as positioned relative to the element 116, so that light emitted from element 116 is directed toward the screen 16. As the light source 100 may be axially spaced from the screen 16, light may be directed axially inwardly from the bezel 20 toward the screen 16—i.e., light rays from the element 116 may be directed away from the cabin 36 and users therein. As will be explained more below, in at least one example, the optic 118 may direct light rays from the element 116 toward a predefined region of the screen 16.

Non-limiting examples of light elements 116 include a light-emitting diode, an incandescent element, etc. Light elements 116 may emit light in any suitable frequency or bandwidth, including: ultraviolet A (UVA) light of 310-390 nanometer (nm) band, UVA light centered at 365 nm, blue light (e.g., within the 400-410 nm band), red light (e.g., in the 670-700 nm band), infrared light (e.g., in 700-800 nm band), and the like. According to one example, the light power at a distance of 18 centimeters from light element 116 may be at least 1 milli-Watt per square centimeter (1 $mW/cm^2$). In other examples, the light power at a distance of 36 centimeters from light element 116 may be at least 1 $mW/cm^2$.

The optic 118 may comprise any suitable optically-transmissive material having any suitable shape—e.g., it may be shaped as a lens, a prism, a waveguide, a light pipe, and the like. For example, optic 118 may comprise acrylic, glass, or any other suitable material. The optic 118 may be carried by the light element 116 (which is coupled to the PCB 120), or both the element 116 and optic 118 may be coupled to PCB 120.

According to one arrangement of the bezel 20, two of light sources 100-114, when actuated, illuminate a pre-defined user-touch region of the screen 16. For example, screen 16 may be sub-divided into four user-touch regions 130, 132, 134, 136 (e.g., a two-by-two matrix or four quadrants of screen 16). By way of example and not limitation, region 130 may concern a user's (e.g., "Paul's") phone, region 132 may concern navigation (e.g., to the user's destination), region 134 may concern climate control settings or data, and region 136 may concern entertainment services (e.g., radio stations) available within cabin 36 (of course, any suitable quantity of user-touch regions may be used, and the input/output data displayed within the respective user-touch regions may vary).

During operation and use, users may touch one of regions 130-136 more than other regions (e.g., based on preference, circumstance, etc.). And computer 40—coupled to display 14—may count and record a quantity of user touches and/or a quantity of user-touches per region 130-136. Accordingly, an inference may be made that the regions 130-136 with the highest quantity of user-touches may be the most contaminated and in need of cleaning (or, e.g., any region having more user-touches than a predetermined threshold may be considered contaminated and in need of cleaning). Accordingly, one or more of the light sources 100-114 may be controlled selectively by computer 40 to illuminate and thereby clean the respective region of the screen 16.

According to one example, when actuated by computer 40, light source pair 108, 100 may illuminate region 130, light source pair 102, 112 may illuminate region 132, light source pair 114, 106 may illuminate region 134, and light source pair 104, 110 may illuminate region 136. According to one example, the light source 100-114 (or pair thereof) is actuated for a predetermined period of time to activate coating 18. For example, where the coating 18 is $TiO_2$, the respective light source(s) may be actuated for a period of ten minutes thereby causing a chemical reaction to occur at the surface 24 of the $TiO_2$ coating for a duration of at least two hours.

By way of example only, one reaction is described. When UVA light is directed from lamp 22 to surface 24, it can kill living organic matter (e.g., germs such as bacteria, viruses, etc.). When the UVA light has a minimum threshold energy at the point of incidence (at surface 24), electrons are released from the $TiO^2$ coating 18. These electrons can combine with water molecules in the air resulting in hydroxyl radicals (OH)—an uncharged form of hydroxide ions ($OH^-$). The hydroxyl radicals can combine with organic matter breaking apart the organic matter's chemical bonds, yielding water ($H_2O$) and carbon dioxide ($CO_2$). Accordingly, organic matter on screen 16 is not only killed, but removed therefrom (e.g., effectively carried away by the water and carbon dioxide molecules)—e.g., leaving surface 24 clear of user-contact or user-touch contaminants such as user bodily fluids. The chemical reaction caused by the light from lamp 22 and coating 18 on screen 16 thus inhibits the dissemination of germs—and can even have a deodorizing effect on the surrounding air.

According to one example, computer 40 may inhibit—at least temporarily—actuation of light sources 100-114 based on one or more predetermined criteria. For example, even though computer 40 may determine that a timer associated with cleaning surface 24 has expired (or even though computer 40 may determine that the surface 24 has been touched a predetermined quantity of times since its last cleaning), computer 40 may delay actuation of light sources 100-114 to minimize user exposure to UVA light. For example, computer 40 may delay actuation: (a) when computer 34 determines an occupant is in cabin 36 and when a day/night detection sensor 140 indicates ambient light is less than a threshold; or (b) when computer 34 determines that an occupant is in cabin 36, sensor 140 indicates ambient light greater than the threshold, and computer 38 indicates that the transmission is not in PARK. Other delay examples also exist.

According to another example, the computer 40 can be triggered to actuate one or more of light sources 100-114 via a switch 142 (FIG. 3). This switch may be part of display 14, or it may be located elsewhere. In at least some examples, a vehicle technician uses switch 142 to clean the display or perform other maintenance tasks.

Other examples and arrangements are also possible. For example, the optic 118 may be formed in the bezel 20, and the light source 116 may be located on an underside of the bezel 20.

Figure 7:
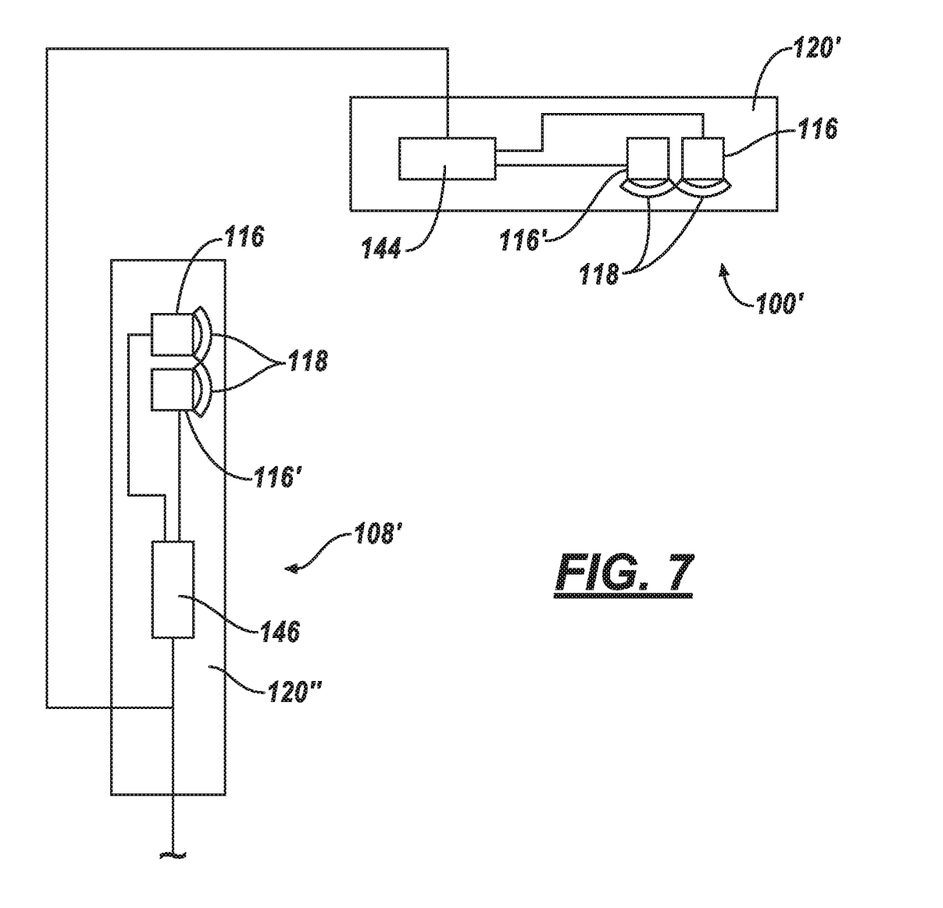
FIG. 7 is a schematic view of two light sources of the display, each light source comprising at least two light elements.

According to another example, any one or more of light sources 100-114 could have multiple light elements. To illustrate, FIG. 7 shows light sources 100' and 108' each having two light elements 116, 116' (e.g., each having a corresponding optic 118 and respectively carried by circuit boards 120', 120"). Elements 116 may emit UVA light, while elements 116' may emit light in another wavelength (e.g., red light, blue light, etc.). For example, certain light wavelengths are known to best visually illuminate blood, semen, saliva, etc.

Each element 116, 116' can be selectively illuminated by computer 40 using switch 144 (light source 100') or switch 146 (source 108'). In this manner, respective elements 116, 116' can be illuminated independently and/or concurrently. According to one example, the computer 40 may actuate elements 116' (e.g., 415 nm) to illuminate contaminants (e.g., blood) on the surface 24 of screen 16 (e.g., to show the user whether the screen 16 is clean or dirty), and then use elements 116 (e.g., 365 nm) to clean the surface 24, as described above.

Figure 8:
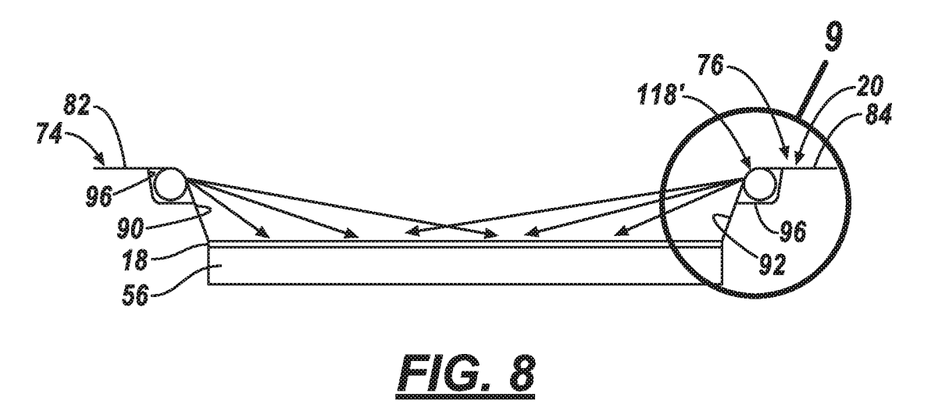
FIG. 8 illustrates a schematic, sectional view of another example of the display.
Figure 9:
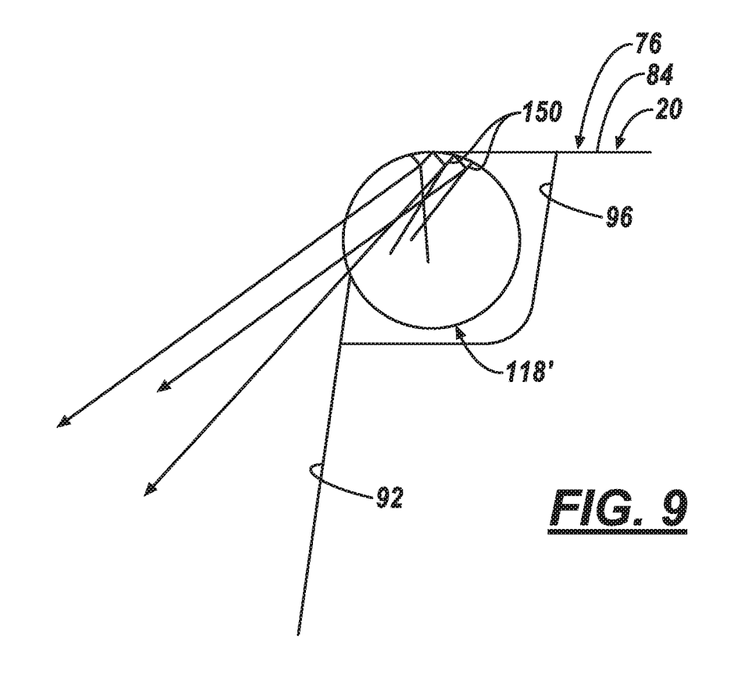
FIG. 9 is an enlarged view of a portion of FIG. 8.

According to another example shown in FIGS. 8-9, the optic of each light source 100-114 may be a longitudinally-extending light pipe 118' having a light element at one or more ends thereof (not shown). For example, the light pipe 118' may extend along at least part of the length of one or more of the members 70-76 (e.g., previously shown in FIG. 6). The light pipe 118' may have one or more facets 150 along the length thereof to internally reflect light out of the pipe 118' and onto the surface 24.

Figure 10:
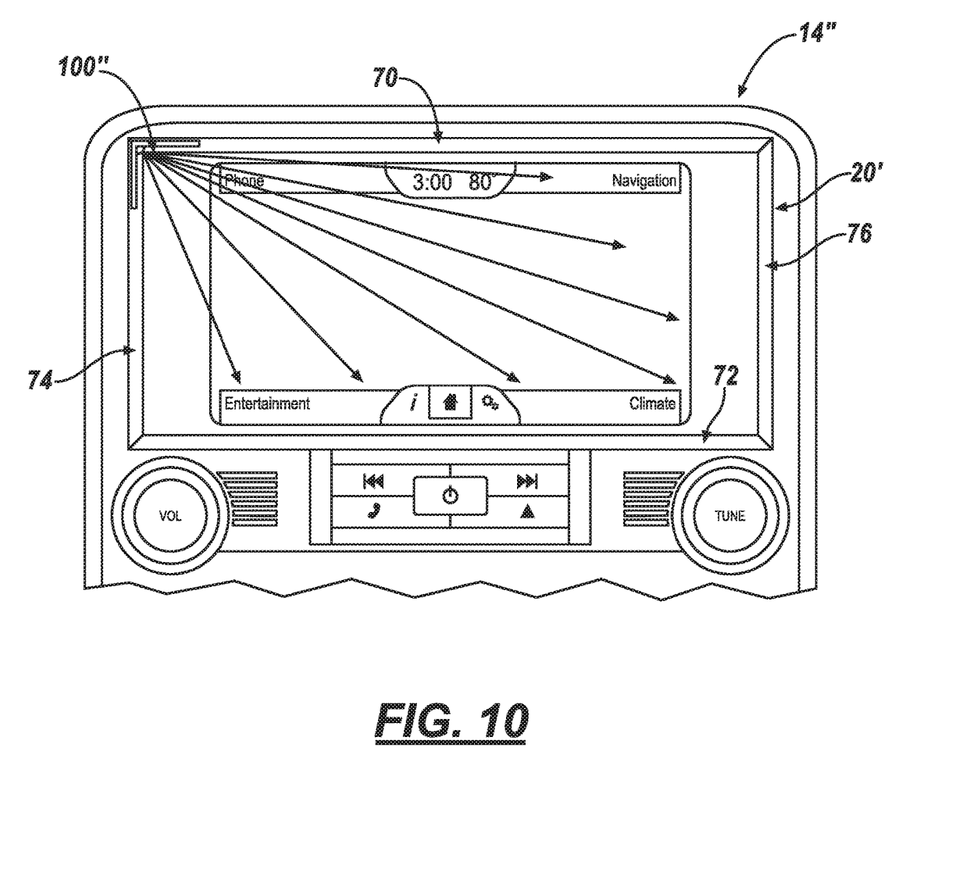
FIG. 10 is a front, schematic view of another example of the display.

FIG. 10 illustrates yet another example of the display. Here, display 14" includes a bezel 20' having a single light source 100". By way of example only, the light source 100" is located in a corner of the bezel 20'—e.g., where members 70 and 74 meet. Of course, a single light source could be arranged differently.

In other examples, the interior cleaning system 10 could be used to clean other surfaces within vehicle 12. For example, other lamps (e.g., such as lamp 22) could be mounted proximate to surfaces often touched by users within the vehicle 12. Similarly, these other lamps could be selectively actuated to clean the respective surfaces thereof.

Thus, there has been described an interior cleaning system for a vehicle. The system includes a display having a screen with a light-sensitive coating and a bezel that includes a lamp. The lamp is arranged to direct light toward the screen. In some examples, light from the lamp includes light in the ultraviolet band that activates the coating to clean the surface thereof.

In general, the computing systems and/or devices described may employ any of a number of computer operating systems, including, but by no means limited to, versions and/or varieties of the Ford SYNC® application, AppLink/Smart Device Link middleware, the Microsoft® Automotive operating system, the Microsoft Windows® operating system, the Unix operating system (e.g., the Solaris® operating system distributed by Oracle Corporation of Redwood Shores, Calif.), the AIX UNIX operating system distributed by International Business Machines of Armonk, N.Y., the Linux operating system, the Mac OSX and iOS operating systems distributed by Apple Inc. of Cupertino, Calif., the BlackBerry OS distributed by Blackberry, Ltd. of Waterloo, Canada, and the Android operating system developed by Google, Inc. and the Open Handset Alliance, or the QNX® CAR Platform for Infotainment offered by QNX Software Systems. Examples of computing devices include, without limitation, an on-board vehicle computer, a computer workstation, a server, a desktop, notebook, laptop, or handheld computer, or some other computing system and/or device.

Computing devices generally include computer-executable instructions, where the instructions may be executable by one or more computing devices such as those listed above. Computer-executable instructions may be compiled or interpreted from computer programs created using a variety of programming languages and/or technologies, including, without limitation, and either alone or in combination, Java™, C, C++, Visual Basic, Java Script, Perl, etc. Some of these applications may be compiled and executed on a virtual machine, such as the Java Virtual Machine, the Dalvik virtual machine, or the like. In general, a processor (e.g., a microprocessor) receives instructions, e.g., from a memory, a computer-readable medium, etc., and executes these instructions, thereby performing one or more processes, including one or more of the processes described herein. Such instructions and other data may be stored and transmitted using a variety of computer-readable media.

A computer-readable medium (also referred to as a processor-readable medium) includes any non-transitory (e.g., tangible) medium that participates in providing data (e.g., instructions) that may be read by a computer (e.g., by a processor of a computer). Such a medium may take many forms, including, but not limited to, non-volatile media and volatile media. Non-volatile media may include, for example, optical or magnetic disks and other persistent memory. Volatile media may include, for example, dynamic random access memory (DRAM), which typically constitutes a main memory. Such instructions may be transmitted by one or more transmission media, including coaxial cables, copper wire and fiber optics, including the wires that comprise a system bus coupled to a processor of a computer. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, or any other medium from which a computer can read.

Databases, data repositories or other data stores described herein may include various kinds of mechanisms for storing, accessing, and retrieving various kinds of data, including a hierarchical database, a set of files in a file system, an application database in a proprietary format, a relational database management system (RDBMS), etc. Each such data store is generally included within a computing device employing a computer operating system such as one of those mentioned above, and are accessed via a network in any one or more of a variety of manners. A file system may be accessible from a computer operating system, and may include files stored in various formats. An RDBMS generally employs the Structured Query Language (SQL) in addition to a language for creating, storing, editing, and executing stored procedures, such as the PL/SQL language mentioned above.

In some examples, system elements may be implemented as computer-readable instructions (e.g., software) on one or more computing devices (e.g., servers, personal computers, etc.), stored on computer readable media associated therewith (e.g., disks, memories, etc.). A computer program product may comprise such instructions stored on computer readable media for carrying out the functions described herein.

The processor is implemented via circuits, chips, or other electronic component and may include one or more microcontrollers, one or more field programmable gate arrays (FPGAs), one or more application specific circuits ASICs), one or more digital signal processors (DSPs), one or more customer integrated circuits, etc. The processor may be programmed to process the sensor data. Processing the data may include processing the video feed or other data stream captured by the sensors to determine the roadway lane of the host vehicle and the presence of any target vehicles. As described below, the processor instructs vehicle components to actuate in accordance with the sensor data. The processor may be incorporated into a controller, e.g., an autonomous mode controller.

The memory (or data storage device) is implemented via circuits, chips or other electronic components and can include one or more of read only memory (ROM), random access memory (RAM), flash memory, electrically programmable memory (EPROM), electrically programmable and erasable memory (EEPROM), embedded MultiMediaCard (eMMC), a hard drive, or any volatile or non-volatile media etc. The memory may store data collected from sensors.

The disclosure has been described in an illustrative manner, and it is to be understood that the terminology which has been used is intended to be in the nature of words of description rather than of limitation. Many modifications and variations of the present disclosure are possible in light of the above teachings, and the disclosure may be practiced otherwise than as specifically described.

The invention claimed is:

1. A display, comprising:
   a screen comprising a cover having a light-sensitive coating on an outwardly-facing side thereof; and
   a bezel extending around a periphery of the screen, the bezel carrying a lamp that comprises a light source and an optic positioned relative to the light source to direct light emitted from the source toward the light-sensitive coating,
   wherein, when actuated, light from the lamp activates the coating.

2. The display of claim 1, wherein, when the lamp is actuated, light is directed axially and radially-inwardly from the bezel and toward the cover.

3. The display of claim 1, wherein the lamp emits an ultraviolet wavelength.

4. The display of claim 1, wherein the coating comprises a material which undergoes a chemical reaction in a presence of light from the lamp.

5. The display of claim 1, wherein the screen comprises an electronics portion that includes: the cover, a capacitive or resistive film, a liquid crystal display (LCD), and a backlight, wherein the film and LCD are sandwiched between the cover and backlight.

6. The display of claim 1, wherein the coating comprises titanium dioxide ($TiO_2$), wherein the lamp emits light at a wavelength within 310-390 nanometers (nm).

7. The display of claim 1, wherein the lamp comprises a plurality of light sources located in the bezel.

8. The display of claim 7, wherein the bezel comprises a plurality of members, wherein each member comprises at least one of the plurality of light sources.

9. The display of claim 8, wherein the screen comprises a matrix of user-touch regions.

10. The display of claim 9, wherein a first member comprises a selectively-actuatable first light source and a selectively-actuatable second light source, wherein a second member comprises a selectively-actuatable third light source and a selectively-actuatable fourth light source, wherein, when selectively-actuated, the second and third light sources illuminate the same user-touch region of the screen.

11. The display of claim 10, wherein, when selectively-actuated, the first light source illuminates a different user-touch region of the screen and the fourth light source illuminates another, different user-touch region of the screen.

12. The display of claim 9, wherein each of the plurality of members comprise at least two light sources, wherein the matrix comprises four user-touch regions, wherein, when selectively-actuated, the respective light sources of each pair of adjacently-located members illuminates one of the user-touch regions.

13. The display of claim 7, wherein at least one of the plurality of light sources comprises a plurality of light elements.

14. The display of claim 13, wherein at least two of the plurality of light elements emit light in different wavelengths, wherein the wavelengths comprise: 310-390 nanometers (nm), 400-410 nm, 670-700 nm, and 700-800 nm.

15. The display of claim 7, wherein, when actuated, light power, incident at the coating, from each of the respective light sources is at least 1 milli-Watt per square centimeter ($mW/cm^2$).

16. The display of claim 1, wherein the screen is a touchscreen.

17. An interior cleaning system for a vehicle, comprising:
   the display of claim 1, wherein the lamp comprises a plurality of light sources; and
   a computer, comprising:
   a processor, and
   memory storing instructions executable by the processor, the instructions comprising: to selectively-actuate the plurality of light sources.

18. The system of claim 17, further comprising a manual switch which, when actuated, triggers at least one of the plurality of light sources to illuminate.

19. The system of claim 17, further comprising an occupancy detection system coupled to the computer that provides an indication of an occupancy state, wherein the instructions further comprise: to temporarily inhibit actuation of the plurality of light sources based on the occupancy state being occupied when an ambient light is less than a threshold.

20. The display of claim 1, wherein the bezel further comprises a cavity, wherein the light source is located within the cavity.

* * * * *